United States Patent
Aida et al.

(10) Patent No.: US 9,885,091 B2
(45) Date of Patent: Feb. 6, 2018

(54) PRIMER SET FOR DETECTING BOVINE LEUKEMIA VIRUS AND USE THEREOF

(71) Applicants: RIKEN, Saitama (JP); RIKEN GENESIS CO., LTD., Tokyo (JP)

(72) Inventors: Yoko Aida, Saitama (JP); Shin-nosuke Takeshima, Saitama (JP); Mayuko Tsunoda, Saitama (JP); Mikio Kawahara, Kanagawa (JP); Susumu Saito, Kanagawa (JP); Yuri Muramatsu, Kanagawa (JP); Yuan Yuan, Kanagawa (JP)

(73) Assignees: RIKEN, Saitama (JP); RIKEN GENESIS CO., LTD., Tokyo (JP)

( * ) Notice: Subject to any disclaimer, the term of this patent is extended or adjusted under 35 U.S.C. 154(b) by 55 days.

(21) Appl. No.: 14/420,720

(22) PCT Filed: Aug. 13, 2013

(86) PCT No.: PCT/JP2013/071883
§ 371 (c)(1),
(2) Date: Feb. 10, 2015

(87) PCT Pub. No.: WO2014/027663
PCT Pub. Date: Feb. 20, 2014

(65) Prior Publication Data
US 2015/0203926 A1  Jul. 23, 2015

(30) Foreign Application Priority Data
Aug. 14, 2012 (JP) ................. 2012-179972

(51) Int. Cl.
| | | |
|---|---|---|
| C12Q 1/68 | (2006.01) |
| A61K 31/7088 | (2006.01) |
| A61P 35/00 | (2006.01) |
| C12Q 1/70 | (2006.01) |
| A61K 31/522 | (2006.01) |

(52) U.S. Cl.
CPC ....... C12Q 1/702 (2013.01); C12Q 2600/158 (2013.01)

(58) Field of Classification Search
CPC ............... C12Q 1/6865; C12Q 1/6809; C12Q 2525/179; C12Q 2525/161; C12Q 2521/119
See application file for complete search history.

(56) References Cited

FOREIGN PATENT DOCUMENTS

| JP | 2004-301518 | | 10/2004 |
| WO | 2012/053666 A1 | | 4/2012 |
| WO | WO2012053666 | * | 4/2012 |
| WO | WO20112053666 | * | 4/2012 |

OTHER PUBLICATIONS

Jimba et al., Retrovirology, 2010, 7:pdf pp. 1-19.*
Buck et al., BioTechniques 27:528-536 (Sep. 1999).*
International Search Report, International Patent Application No. PCT/JP2013/071883, dated Nov. 5, 2013.
International Preliminary Report on Patentability, International Patent Application No. PCT/JP2013/071883, dated Feb. 26, 2015.
Panei CJ, et al., "Estimation of bovine leukemia virus (BLV) proviral load harbored by lymphocyte subpopulations in BLV-infected cattle at the subclinical stage of enzootic bovine leucosis using BLV-CoCoMo-qPCR.", BMC Veterinary Research, 2013, vol. 9, No. 95.
Jimba M. et al., "BLV-CoCoMo-qPCR: a useful tool for evaluating bovine leukemia virus infection status.", BMC Veterinary Reserch, 2012, vol. 8, No. 167.
Jimba M. et al., "BLV-CoCoMo-qPCR: Quantitation of bovine leukemia virus proviral load using the CoCoMo algorithm.", Retrovirology, 2010, vol. 7, No. 91.
European Search Report, European Patent Application No. 13879359.1, dated Mar. 31, 2016.

* cited by examiner

Primary Examiner — Barry A Chestnut
(74) Attorney, Agent, or Firm — Casimir Jones, SC

(57) ABSTRACT

A forward primer of a primer set in accordance with the present invention for detecting BLV is a mixture of (1) a first primer consisting of a polynucleotide including 15 or more successive bases including the 16th C in the base sequence of SEQ ID NO: 1 and (2) a second primer consisting of a plurality of kinds of polynucleotides including at least the first to 15th bases in the base sequence of SEQ ID NO: 2. Two or more of M, N, Y, K, and D which are included in the second primer are each a degenerate base which specifies two or more kinds of bases, and the second primer includes at least 10 kinds of polynucleotides including at least the first to 15th bases in the base sequences of SEQ ID NOs: 3 to 12.

6 Claims, 4 Drawing Sheets

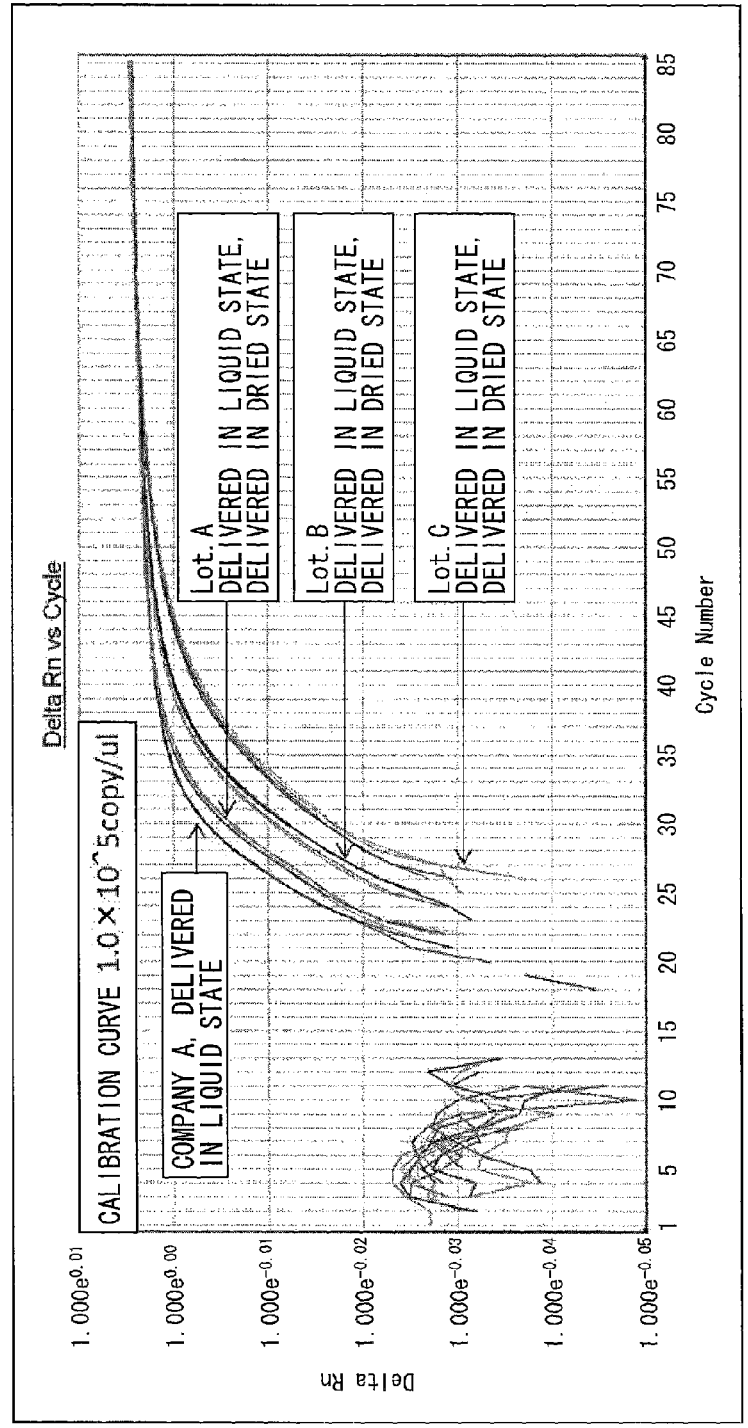
F I G. 2

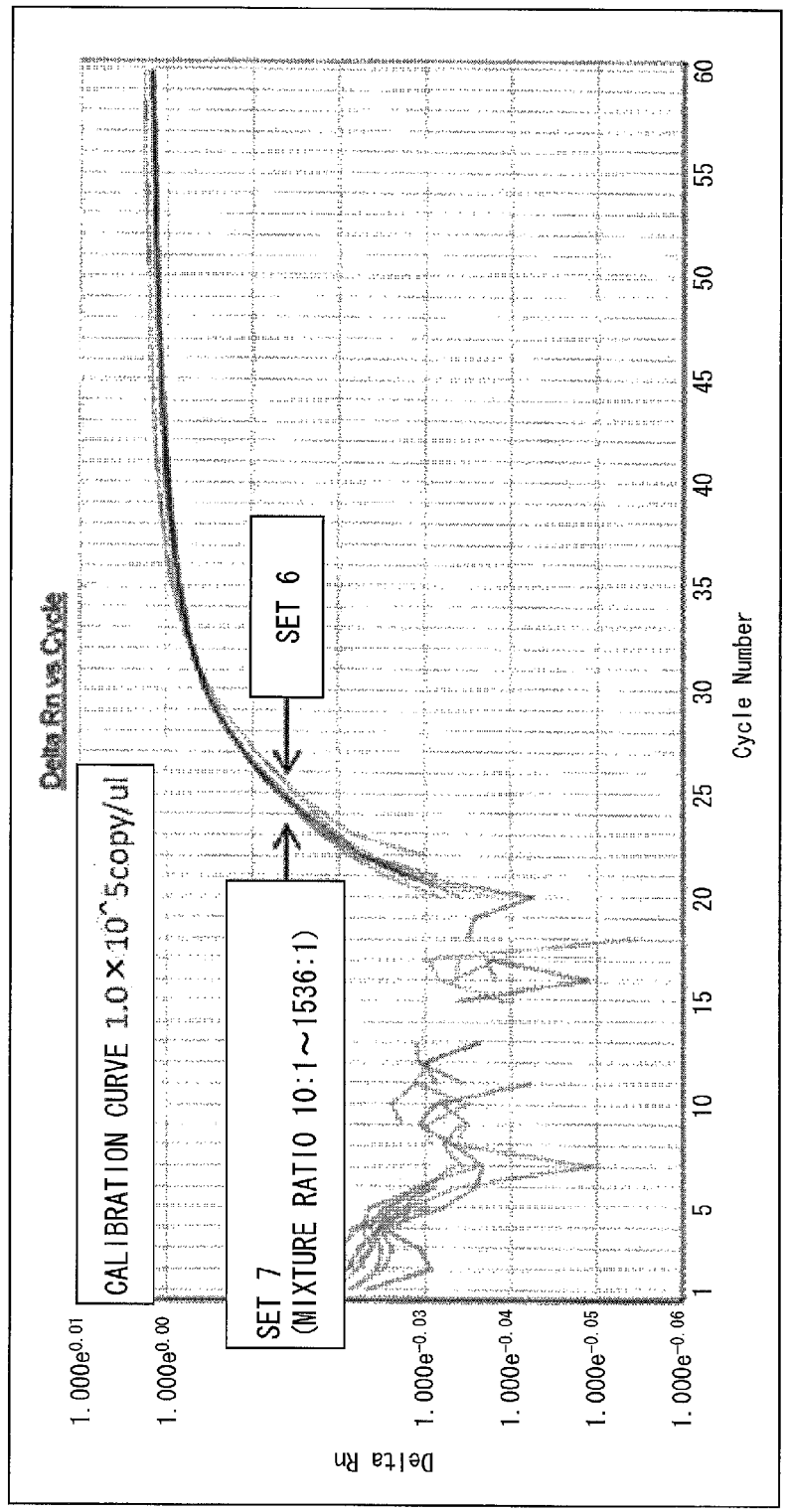
F I G. 4

SEQUENCE LISTING

<160> NUMBER OF SEQ ID NOS: 21

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
caccctgagc tgctgcacct cacct                                          25

<210> SEQ ID NO 2
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n = a, c, g or t

<400> SEQUENCE: 2
mnmycykdag ctgctgayyt cacct                                          25

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
acaccctgag ctgctgacct cacct                                          25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
acatcctgag ctgctgacct cacct                                          25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
acaccctgag ctgctgacct cacct                                          25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cactcctgag ctgctgacct cacct                                          25

```
<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
acaccctgag ctgctgacct cacct                                              25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
acaccctgag ctgctgacct cacct                                              25

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
ataccctgag ctgctgattt cacct                                              25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
agaccctgag ctgctgacct cacct                                              25

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
caccctgtag ctgctgacct cacct                                              25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
acaccctaag ctgctgacct cacct                                              25

<210> SEQ ID NO 13
<211> LENGTH: 25
<212> TYPE: DNA
<213> ORGANISM: Artificial Sequence
<220> FEATURE:
<223> OTHER INFORMATION: Primer
<220> FEATURE:
```

-continued

```
<221> NAME/KEY: misc_feature
<222> LOCATION: (2)..(2)
<223> OTHER INFORMATION: n = a, c, g or t

<400> SEQUENCE: 13
mnmycykdrs yksyksayyt cacct                                            25

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
tacctgmcss ctkscggata gccga                                            25

<210> SEQ ID NO 15
<211> LENGTH: 14
<212> TYPE: DNA
<213> ORGANISM: Artificial Sequence
<220> FEATURE:
<223> OTHER INFORMATION: Probe

<400> SEQUENCE: 15
tgtgtgccct gggc                                                        14

<210> SEQ ID NO 16
<211> LENGTH: 15
<212> TYPE: DNA
<213> ORGANISM: Artificial Sequence
<220> FEATURE:
<223> OTHER INFORMATION: Probe

<400> SEQUENCE: 16
ctcagctctc ggtcc                                                       15

<210> SEQ ID NO 17
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (7)..(7)
<223> OTHER INFORMATION: n = a, g, c, or t

<400> SEQUENCE: 17
aatccmnmyc ykdagctgct gayytcacct                                       30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
atccacaccc tgagctgctg cacctcacct                                       30

<210> SEQ ID NO 19
<211> LENGTH: 31
<212> TYPE: DNA
<213> ORGANISM: Artificial Sequence
<220> FEATURE:
<223> OTHER INFORMATION: Primer
```

```
<400> SEQUENCE: 19
ttgccttacc tgmcssctks cggatagccg a                              31

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
cccagagacc acagagcctg c                                         21

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
cccaccagag ccacaatca                                            19
```

US 9,885,091 B2

PRIMER SET FOR DETECTING BOVINE LEUKEMIA VIRUS AND USE THEREOF

CROSS-REFERENCE TO RELATED APPLICATIONS

The present application is a U.S. 371 National Stage Entry of pending International Patent Application No. PCT/JP2013/071883, international filing date Aug. 13, 2013, which claims priority to JP Patent Application No. 2012-179972, filed Aug. 14, 2012, the contents of which are incorporated by reference in their entireties.

TECHNICAL FIELD

The present invention relates to a novel primer set for detecting bovine leukemia virus (BLV), a novel kit for detecting BLV, and a novel method for detecting BLV.

BACKGROUND ART

Bovine leukemia virus (BLV) is a retrovirus which is the most closely related to human T-cell leukemia virus (HTLV) and induces enzootic bovine leukosis (EBL), which is B lymphoma. In recent years, the number of cattle infected with BLV is increasing and, in proportion to this, the number of cattle developing BLV is increasing.

BLV has a large number of variants, and there is a demand for a tool that can detect the variants collectively in determining whether or not BLV infection is occurring. For example, Non-patent Literature 1 discloses a degenerate primer for BLV detection, capable of detecting major variants of BLV and unknown variants of BLV.

CITATION LIST

Non-Patent Literature

Non-Patent Literature 1
Jimba, M., S. N. Takeshima, K. Matoba, D. Endoh, and Y. Aida. 2010. BLV-CoCoMo-qPCR: Quantitation of bovine leukemia virus proviral load using the CoCoMo algorithm. Retrovirology 7:91.

SUMMARY OF INVENTION

Technical Problem

However, the degeneracy of the degenerate primer disclosed in Non-patent Literature 1 is very high, so that an advanced technique is required in manufacture of the degenerate primer in order for the manufactured degenerate primer to have high quality.

The invention of the subject application is made in view of the circumstances above. An object of the invention of the subject application is to provide: a primer set for detecting BLV which primer set is both easily manufactured and capable of detecting major variants of BLV and unknown variants of BLV; a kit for detecting BLV; and a method for detecting BLV.

Solution to Problem

That is, the present invention encompasses the following invention.

A primer set capable of amplifying, through polymerase chain reaction, a DNA fragment derived from bovine leukemia virus, consisting of a combination of a forward primer and a reverse primer, the forward primer being a mixture of (1) a first primer consisting of a polynucleotide including 15 or more successive bases including the 16th cytosine in the base sequence of SEQ ID NO: 1 and (2) a second primer consisting of a plurality of kinds of polynucleotides including at least the first to 15th bases in the base sequence of SEQ ID NO: 2, in the SEQ ID NO: 2, a base M representing A or C, a base N representing A, C, G, or T, a base Y representing C or T, a base K representing G or T, a base D representing A, G, or T, two or more bases among the base M, the base N, the base Y, the base K, and the base D which are included in the second primer each being a degenerate base which specifies two or more kinds of bases, the second primer including at least 10 kinds of polynucleotides including at least the first to 15th bases in the base sequences of SEQ ID NOs: 3 to 12.

Advantageous Effects of Invention

The present invention makes it possible to provide a primer set and the like for detecting BLV which are easily manufactured.

BRIEF DESCRIPTION OF DRAWINGS

FIG. 2 is a view showing another example of an amplification plot in Reference Example 1.
FIG. 4 is a view showing an amplification plot in Example 3.

DESCRIPTION OF EMBODIMENTS

Figure 1:
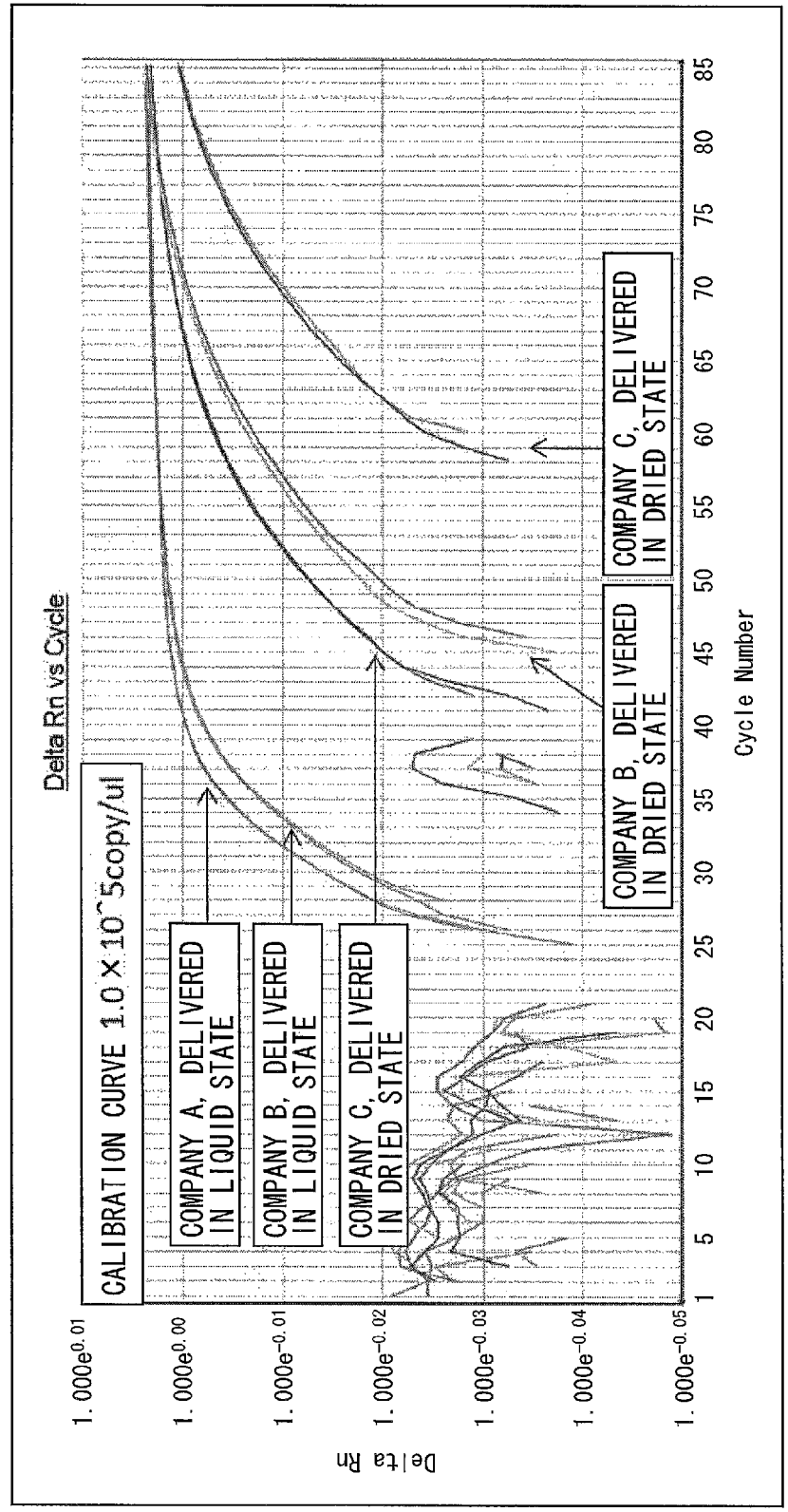
FIG. 1 is a view showing an example of an amplification plot in Reference Example 1.

The following description will discuss in detail an embodiment of the present invention.

[1: Primer Set]

A primer set in accordance with the present invention is capable of amplifying, through polymerase chain reaction (PCR), a DNA fragment derived from bovine leukemia virus (BLV). That is, the primer set in accordance with the present invention (i) hybridizes with DNA derived from BLV or a fragment of the DNA and (ii) amplifies, through PCR, the DNA fragment having a predetermined size.

The primer set preferably has a property of being capable of selectively amplifying, through PCR, a DNA fragment derived from BLV. Note here that 'capable of selectively amplifying' means that, in a case where PCR is performed on a predetermined sample with use of the primer set, a DNA fragment derived from BLV is exclusively obtained as an amplification product but substantially no DNA fragments derived from many other organisms (in particular, a host organism of BLV such as cattle) are obtained as amplification products.

Note that BLV to which the primer set in accordance with the present invention is applied can be in the form of provirus DNA incorporated in a genome of a host, or in the form of cDNA corresponding to a transcription product of a provirus. In particular, provirus DNA incorporated in a genome of a host is the more preferable form.

The primer set in accordance with the present invention is specifically as follows.
A primer set which is capable of amplifying, through polymerase chain reaction, a DNA fragment derived from bovine leukemia virus and consists of a combination of a forward primer and a reverse primer, wherein: the forward primer is a mixture of (1) a first primer consisting of a polynucleotide including 15 or more successive bases including the 16th cytosine in the base sequence of SEQ ID NO: 1 and (2) a second primer consisting of a plurality of kinds of polynucleotides including at least the first to 15th bases in the base sequence of SEQ ID NO: 2; in SEQ ID NO: 2, a base M represents A (adenine) or C (cytosine), a base N represents A, C, G (guanine), or T (thymine), a base Y represents C or T, a base K represents G or T, and a base D represents A, G, or T; two or more of the base M, the base N, the base Y, the base K, and the base D included in the second primer are each a degenerate base which specifies two or more kinds of bases; and the second primer includes at least 10 kinds of polynucleotides including at least the first to 15th bases in the base sequences of SEQ ID NOs: 3 to 12. In the Description, a 'base' refers to a nucleic acid base unless otherwise specifically noted.

Each of the first primer and the second primer should have a length which is not less than 15 base length, preferably in a range of not less than 15 base length but not more than 50 base length, more preferably in a range of not less than 18 base length but not more than 35 base length, further more preferably in a range of not less than 20 base length but not more than 35 base length, particularly preferably in a range of not less than 23 base length but not more than 30 base length. Note that SEQ ID NOs: 1 to 12 each show a sequence of 25 bases, but since design of the sequence of the 25 bases is based on a known base sequence of BLV, a base sequence connected to the front or behind of the 25 bases, if necessary, may be designed on the basis of the known base sequence of BLV so as to hybridize with the known base sequence derived from BLV.

The second primer preferably consists of a plurality of kinds of polynucleotides including at least the first to 18th bases in the base sequence of SEQ ID NO: 2, in a case where the second primer has not less than 18 base length. Further, the second primer preferably consists of a plurality of kinds of polynucleotides including at least the first to 19th bases in the base sequence of SEQ ID NO: 2, in a case where the second primer has not less than 19 base length.

'The base M, the base N, the base Y, the base K, and the base D are included' in the second primer, which is a mixture of a plurality of primers, means a state in which, for example, in the case of the base M, a base corresponding to the base M is A or C when the second primer is considered as a whole. That is, for example, A is the base corresponding to the base M in one primer(s) constituting the second primer, C is the base corresponding to the base M in another primer(s) constituting the second primer, and neither T nor G occurs as a base corresponding to the base M. The same applied to the other bases: the base N, the base Y, the base K, and the base D. Note that, as described later, the base M, the base N, the base Y, the base K, and the base D may be included as a degenerate base or may be included as a separate base.

'Two or more of the base M, the base N, the base Y, the base K, and the base D are each a degenerate base which specifies two or more kinds of bases' in the second primer means that all the possible combinations of kinds of bases that can be taken between two or more bases which are degenerate bases occur in the second primer. Specifically, for example, in a case where (i) the first base M and the second base N in the base sequence of SEQ ID NO: 2 are degenerate bases, (ii) the base M specifies A and C as degenerate bases, and (iii) the base N also specifies A and C as degenerate bases, the second primer is arranged so that all the degeneration patterns AA, AC, CA, and CC are included in the second primer (that is, so that degenerate primers to which the first base and the second base are involved are included in the second primer). Note that the second base N needs to take G and T, but G and T occur in the second primer as separate bases, not as degenerate bases. To occur as separate bases means that, instead of all the possible combinations, only a part of all the possible combinations occur (e.g., AG and AT are the only combinations of the first base and the second base). Similarly, in a case where (i) the first base M and the second base N in the base sequence of SEQ ID NO: 2 are degenerate bases, (ii) the base M specifies A and C as degenerate bases, and (iii) the base N specifies A, C, and G as degenerate bases, the second primer is arranged so that 2×3=6 patterns of degeneration are included (that is, degenerate primers to which the first base and the second base are involved are included) and T taken by the second base N occurs as a separate base. This idea is also applied to a case where three or more bases are degenerate bases and a case where bases that are not adjacent to each other (e.g., the first base M and the third base M in SEQ ID NO: 2) are degenerate bases. More specifically, in a set 5 shown in Examples, the first base M and the third base M in SEQ ID NO: 2 occur in the second primer, without being degenerated as separate bases, the second base N (representing A, C, G, or T) occurs in the second primer as a separate base A and a degenerate base B (representing C, G, and T), and the fourth base Y occurs in the second primer as a degenerate base Y (the fifth base and bases subsequent to the fifth base are also similarly designed, and detailed descriptions on these bases therefore will be omitted).

In a particularly preferred mode of the second primer, all of the base M, the base N, the base Y, the base K, and the base D included in the second primer are degenerate bases each of which specifies all the possible kinds of bases. That is, in order to specify all the possible kinds of bases, the base M occurs in the second primer (mixture) as a degenerate base specifying A and C, the base N occurs in the second primer as a degenerate base specifying A, C, G, and T, the base Y occurs in the second primer as a degenerate base specifying C and T, the base K occurs in the second primer as a degenerate base specifying G and T, and the base D occurs in the second primer as a degenerate base specifying A, G, and T. More specifically, the particularly preferred mode corresponds to a set 6 and a set 7 shown in Examples.

The forward primer is a mixture of a plurality of kinds of polynucleotides (primers). A mixture ratio of the plurality of kinds of polynucleotides is not particularly limited, but preferably the forward primer is a mixture of substantially equal parts of the respective polynucleotides. The mixture of substantially equal parts means that a quantity ratio (substantially equal in meaning to molar ratio) of a polynucleotide whose content is the lowest to a polynucleotide whose content is the highest is within a range of 1:1 to 1:1.3, preferably within a range of 1:1 to 1:1.15.

As described above, the forward primer is constituted by the first primer and the second primer which always includes 10 kinds of polynucleotides including at least the first to 15th bases in the base sequences of SEQ ID NOs: 3 to 12. These 11 kinds of polynucleotides amplify major 11 kinds of known sequences of BLV. Further, as described above, the second primer further includes a degenerate primer defined by the degenerate base, and is capable of amplifying known sequences of BLV other than the 11 kinds above and unknown sequences of BLV. Further, a maximum degeneracy is 1536 (2×4×2×2×2×2×3×2×2) in the forward primer, so that the forward primer can be produced significantly more easily as compared with the degenerate primer (degeneracy: 393216) disclosed in Non-patent Literature 1.

Note that the reverse primer can be obtained by designing the reverse primer with reference to a sequence common to a plurality of kinds of BLV, or by using, as appropriate, the reverse primer for BLV amplification described in Non-patent Literature 1. The reverse primer should, like the forward primer, have a length of not less than 15 base length, preferably within a range of not less than 15 base length but not more than 50 base length, more preferably within a range of not less than 18 base length but not more than 35 base length, and further more preferably within a range of not less than 20 base length but not more than 35 base length, particularly preferably not less than 23 base length but not more than 35 base length. It may be preferable that the reverse primer be designed so that a PCR amplified fragment obtained as a result of conducting PCR has a size of approximately 100 bp to 500 bp. A preferred example of the reverse primer is a polynucleotide which (i) includes at least the seventh to 14th bases in the base sequence of SEQ ID NO: 14 and (ii) has a length of not less than 15 base length but less than 50 base length.

A quantity ratio (substantially equal in meaning to molar ratio) of the forward primer and the reverse primer which are included in the primer set is not specifically limited, but a concentration of the forward primer is preferably within a range of five times to 15 times a concentration of the reverse primer, more preferably with in a range of eight times to 12 times the concentration of the reverse primer.

Further, PNA (peptide nucleic acid) may be included among nucleotides constituting each primer.

The primer set in accordance with the present invention can be synthesized by a standard method known in the art. Further, conditions under which PCR is reacted with use of the primer set in accordance with the present invention are not particularly limited. In an example corresponding to a case where 2-step PCR is used, a temperature at which a denaturation step is carried out is set, for example, within a range of 93° C. to 96° C., preferably within a range of 94° C. to 95° C. A temperature at which an annealing and extension step is set, for example, within a range of 58° C. to 69° C., preferably within a range of 59° C. to 63° C. A reaction time in the denaturation step is set, for example, within a range of 14 sec to 25 sec, preferably within a range of 14 sec to 20 sec. A reaction time of the annealing and extension step is set, for example, within a range of 25 sec to 1 min, preferably within a range of 28 sec to 35 sec. Further, the number of cycles (cycle number) is set, for example, within a range of 20 cycles to 100 cycles, preferably within a range of 55 cycles to 85 cycles, more preferably within a range of 55 cycles to 65 cycles.

[2: Kit for Detecting BLV]

A kit in accordance with the present invention for detecting BLV includes the above-described primer set in accordance with the present invention. The kit for detecting BLV is used for detection of BLV, including determination of whether or not BLV is present. The kit for detecting BLV may further include at least one of the followings as necessary: (1) various reagents and tools for PCR (polymerase, PCR buffer, dNTPs, pipette, etc.), (2) various reagents and tools for preparing an analyte which contains DNA and on which PCR (test tube, buffer, etc.) is to be performed, (3) various reagents and tools for analyzing a PCR amplified fragment (electrophoresis gel material, pipette, etc.), 4) for further detailed analysis, a PCR primer set which is capable of amplifying specific BLV, 5) an instruction manual for the kit, and the like.

[3: Method for Detecting BLV]

A method in accordance with the present invention for detecting BLV includes the following steps:

(a) preparing, from a subject sample, an analyte containing DNA;

(b) performing polymerase chain reaction on the analyte with use of the primer set in accordance with the present invention; and (c) detecting an amplified fragment obtained by the step (b).

The following describes each of the steps (a) to (c).

(1) Step (a)

The step (a) is a step of preparing, from a subject sample, an analyte containing DNA. Note that 'subject sample' means a sample from which BLV is to be detected. The subject sample can be anything that may contain BLV. The subject sample is, for example, an analyte derived from a mammal, more specifically, an analyte derived from a body fluid (in particular, blood or milk) or tissue of a bovid mammal which can get infected with BLV, such as cattle, buffalo, sheep, or goat. Or alternatively, the subject sample can be a cultured cell derived from mammals of many types which can get infected with BLV in vitro, such as cattle, sheep, cat, bat, human, and the like. The analyte containing DNA can be prepared by a standard method known in the art, depending on a type of the subject sample. For example, in a case where provirus DNA of BLV is the subject of detection, genome DNA can be extracted from the subject sample by a standard method known in the art. In a case where a transcription product (RNA) of the provirus DNA is the subject of detection, total RNA can be extracted from the subject sample by a standard method known in the art, and the total RNA can be reverse transcribed into cDNA by a standard method known in the art to thereby obtain the analyte.

(2) Step (b)

The step (b) is a step of performing, with use of the primer set in accordance with the present invention, PCR on the analyte obtained in the step (a). The PCR in the step (b) can be carried out in accordance with a standard method known in the art. In a case where BLV is contained in the analyte, the step (b) enables to obtain a PCR amplified fragment derived from BLV and having, at both ends of the PCR amplified fragment, a base sequence of the primer used.

(3) Step (c)

The step (c) is a step of detecting presence or absence of the PCR amplified fragment obtained in the step (b). The presence or absence of the PCR amplified fragment (amplicon) can be checked by a standard method known in the art. For example, the presence or absence of the PCR amplified fragment and a size of the PCR amplified fragment can be checked by performing electrophoresis. Further, quantitative detection of the PCR amplified fragment can be carried out as necessary. Note that the steps (b) and (c) are preferably carried out in one step by performing real-time PCR.

In a case where a result of checking the presence or absence of the PCR amplified fragment shows that the PCR amplified fragment is present, it can be concluded that BLV is present in the subject sample. In a case where checking the presence or absence of the PCR amplified fragment shows that the PCR amplified fragment is absent, it can be concluded that no BLV is present in the subject sample.

[4: Method of Designing Forward Primer]

The forward primer included in the primer set in accordance with the present invention is designed as follows, for example. In order to make it possible to detect 11 kinds of major BLVs shown in the Examples, the first primer is designed independently of other primers, on the basis of the base sequence of SEQ ID NO: 1. The base sequence of SEQ ID NO: 1 is a base sequence which includes a mutated site of BLV called DQ287255 (see below for references and sources, etc.).

The second primer is designed as follows from 10 kinds of base sequences (respectively corresponding to SEQ ID NOs: 3 to 12 in this order) which include mutated sites of EF600696, DQ287261, D00647, DQ287257, AF257515, DQ287260, DQ288220, M38278, DQ287259, and DQ288193 (see below for references and sources, etc.), which are remaining 10 kinds of BLVs. First, 10 kinds of base sequences are categorized into one or more groups. The grouping is performed so that each group always includes a plurality of kinds of base sequences. For example, in a case where only one group is to be made, all of the 10 kinds of base sequences are included in the same group. In a case where two groups are to be made, the 10 kinds of base sequences are divided into 2 and 8 kinds of base sequences, 3 and 7 kinds of base sequences, 4 and 6 kinds of base sequences, or 5 and 5 kinds of base sequences. Then, comparison of sequences is performed between base sequences belonging to the same group (whether or not n-th (n is an integer of 1 to 125) bases in the respective base sequences are identical is determined), and a degenerate primer which specifies, as degenerate bases, only bases that are different between sequences is designed. That is, in a case where only one group is to be made, a single degenerate primer constitutes the second primer, and in a case where two groups are to be made, two degenerate primers constitute the second primer.

The forward primer which is constituted as described above includes nucleotides derived from SEQ ID NO: 1 and SEQ ID NOs: 3 to 12 and, accordingly, is capable of detecting the 11 major BLVs. Further, since the second primer is a degenerate primer, the second primer is capable of detecting BLV other than the 11 major BLVs. Further, since a primer for BLV called DQ287255 was designed in a form that is not a degenerate primer, degeneracy was significantly suppressed. The significant suppression of degeneracy means that production of the degenerate primer with stable quality is greatly facilitated.

(References and Sources Related to BLV Sequence Information)

DQ287255: Hirsch, C., Barbosa-Stancioli, E. F., Camargos, M. F., Reis, J. K. P., and Leite, R. C., Bovine Leukemia Virus LTR: Genetic Variability and Phylogeny of Brazilian Samples, Direct Submission Submitted (10 Nov. 2005) (Source A)

EF600696: Rovnak, J., Boyd, A. L., Casey, J. W., Gonda, M. A., Jensen, W. A., and Cockerell, G. L. 1993, Pathogenicity of molecularly cloned bovine leukemia virus. J. Virol. 67, 7096-7105 (Source B)

DQ287261: (Source A)

D00647: Coulston, J., Naif, H., Brandon, R., Kumar, S., Khan, S., Daniel, R. C., and Lavin, M. F., Molecular cloning and sequencing of an Australian isolate of proviral bovine leukaemia virus DNA: comparison with other isolates. 1990, J. Gen. Virol. 71, 1737-1746 (Source C)

DQ287257: (Source A)

AF257515: Dube, S., Dolcini, G., Abbott, L., Mehta, S., Dube, D., Gutierrez, S., Ceriani, C., Esteban, E., Ferrer, J., and Poiesz, B., The complete genomic sequence of a BLV strain from a Holstein cow from Argentina. 2000, Virology 277, 379-386 (Source D)

DQ287260: (Source A)

DQ288220: Zhao, X., Jimenez, C., Sentsui, H., and Buehring, G. C., Sequence polymorphisms in the long terminal repeat of bovine leukemia virus: evidence for selection pressures in regulatory sequences. 2007, Virus Res. 124, 113-124 (2007) (Source E)

M38278: Ivanova, M. N., Bychko, V. V., Meldrais, Ia. A., Tsimanis, A. Iu., and Dresher, B., Primary structure of the 3'-terminal region of the cloned DNA of the bovine leukemia virus. 1986, Bioorg. Khim. 12, 420-423 (Source F)

DQ287259: (Source A)

DQ288193: (Source E).

This application claims priority on Patent Application No. 2012-179972 (basic application) filed in Japan on Aug. 14, 2012, the entire contents of which are hereby incorporated by reference. All documents cited in this specification are hereby incorporated by reference in their entireties.

EXAMPLES

The following description will discuss the present invention in further detail with reference to Reference Examples and Examples.

Reference Example 1

With reference to Non-patent Literature 1, amplification of a gene fragment of BLV by real-time PCR reaction was conducted under the following conditions with use of (i) the base sequence of SEQ ID NO: 13 (base sequence: MNMYCYKDRSYKSYKSAYYTCACCT) as a forward primer for detecting BLV, and (ii) the base sequence of SEQ ID NO: 14 (base sequence: TACCTGMCSSCTKSCGGATAGCCGA) as a reverse primer. Note that in SEQ ID NOs: 13 and 14, M is a degenerate base representing A and C, N is a degenerate base representing A, C, G, and T, Y is a degenerate base representing C and T, K is a degenerate base representing G and T, D is a degenerate base representing A, G, and T, R is a degenerate base representing A and G, and S is a degenerate base representing G and C, and degeneracy of the forward primer is 393216. Note that liquid products (delivered in a liquid state) or dried products (delivered in a dried state) manufactured by three different companies (companies A to C) were used as the forward primer, and a liquid product was used as the reverse primer. Note that in the Reference Examples and the Examples, a liquid product refers to oligo-DNA which is delivered in a state of an aqueous solution obtained by dissolving oligo-DNA in a predetermined liquid (10 mM Tris-HCL, 1 mM EDTA (pH 8.0)), and a dried product dried product refers to oligo-DNA which is delivered in a dried state.

<Preparation of Analyte for Real-Time PCR>

A cell line KU-1, which is a Bovine B-cell leukemia cell line and from which no leukemia virus is produced but BLV is detected in an amount of about of $1 \times 10^4$ copy/μL, was cultured to collect $1 \times 10^7$ cells. From the cultured cells thus obtained, genome DNA was extracted with use of the Wizard® Genomic DNA Purification Kit (Promega) and was dissolved in TE buffer to collect a genome DNA solution in an amount of about 50 ng/μL, 100 μg. The genome DNA solution was used as a highly-concentrated analyte (HA) sample for real-time PCR.

The calibration curve was created in the following manner. The BoLA-DRA gene/pBluescript+II and the BLV-LTR gene/pBluescript+II, which were produced in Non-patent Literature 1, were purified with use of the QUIAGEN Plasmid Maxi Kit and then were adjusted to have a linear shape with use of restriction enzyme XhoI. Subsequently, O.D values were measured and DNA quantification was performed with use of Quant-iT® PicoGreen® dsDNA Reagent and Kits (Life Technologies) to calculate the number of moles. A resultant 1 cut calibration curve plasmid whose concentration was known was diluted in a range of 1 mol/μL (1 copy) to 1×10$^7$ mol/μL (10$^7$ copy) and was used as a calibration curve of quantitative PCR.

<Reaction Conditions for Real-Time PCR and Data Analysis Conditions>

In the sequence of a TaqMan probe used in the real-time PCR, VIC-DRA for DRA detection was [5'-VIC-TGTGT-GCCCTGGGC-NFQ-MGB-3': SEQ ID NO: 15] and FAM-BLV for BLV detection was [5'-FAM-CTCAGCTCTCG-GTCC-NFQ-MGB-3': SEQ ID NO: 16]. The real-time PCR was performed under the following PCR reaction conditions with use of the Applied Biosystems 7500 Fast real-time PCR system.

Composition of Reaction Solution for PCR:
(1) Reaction Solution for DRA (in 20 μL)
A forward primer for DRA detection and a reverse primer for DRA detection: 85 nM each
(The sequence of the forward primer for DRA detection (SEQ ID NO: 20): CCCAGAGACCACAGAGCCTGC)
(The sequence of the reverse primer for DRA detection (SEQ ID NO: 21): CCCACCAGAGCCACAATCA)
2×TaqMan Gene Expression Master mix: 10 μL
Genome DNA derived from cattle: 150 μg
(2) Reaction Solution for BLV (in 20 μL)
A forward primer for BLV detection: 850 nM
A reverse primer for BLV detection: 85 nM
2×TaqMan Gene Expression Master mix: 10 μL
Genome DNA derived from cattle: 150 μg PCR reaction conditions (common between DRA detection and BLV detection):
A reaction was conducted at 50° C. for two min, then at 95° C. for 10 min, and then 85 cycles of reaction, each cycle made up of a reaction at 95° C. for 15 sec and a reaction at 60° C. for one (1) min, were conducted.

[Results]

FIGS. 1 and 2 each show a relation between the number of cycles (cycle number) of the real-time PCR (horizontal axis) and delta-Rn (vertical axis) (what is called an amplification plot). As known from FIG. 1, variation in quality was observed both among the liquid products manufactured by the different companies and among the dried products manufactured by the different companies. FIG. 2 shows comparison between (i) the liquid product of the company A (indicated as 'COMPANY A, DELIVERED IN LIQUID STATE') which exhibits the highest quality in FIG. 1 and (ii) different lots A to C (a liquid product and a dried product) of the company A. As shown in FIG. 2, variation in quality was observed among different lots of the same product.

Example 1

First, a gene fragment of BLV was amplified by real-time PCR reaction under the following conditions with use of (i) a mixture of Nos. 5-1 to 5-3 (hereinafter, 'set 5') of Table. 1 below as a forward primer for BLV detection and (ii) the sequence of SEQ ID NO: 14 (a sequence identical to that in Reference Example 1) as a reverse primer for BLV detection. Note that in the forward primer, B is a degenerate base representing A, C, and G, Y is a degenerate base representing C and T, K is a degenerate base representing G and T, and R is a degenerate base representing A and G, and degeneracy of the forward primer is 64 (3×2×2×2×2=48 in the sequence of No. 5-2 and 2×2×2×2=16 in the sequence of No. 5-3 in Table. 1). Note that a liquid product was used as the forward primer and a liquid product was used as the reverse primer.

TABLE 1

| No. | Sequence | Mixture ratio | Remark |
|---|---|---|---|
| 5-1 | CACCCTGAGCTGCTGCACCTCACCT | 1 | Corresponding to SEQ ID NO: 1 |
| 5-2 | ABAYCCTRAGCTGCTGAYYTCACCT | 8 | Degenerate primer which specifies only different bases as a degenerate base in a group made up of SEQ ID NOs: 3 to 5, 7 to 10, and 12 |
| 5-3 | CACYCYKKAGCTGCTGACCTCACCT | 2 | Degenerate primer which specifies only different bases as a degenerate base in a group made up of SEQ ID NOs: 6 and 11 |

Further, a gene fragment of BLV was amplified by real-time PCR reaction under the following conditions, with use of (i) a mixture of Nos. 6-1 and 6-2 (hereinafter, 'set 6') of Table. 2 below as a forward primer for BLV detection and (ii) the sequence of SEQ ID NO: 14 (the same as in Reference Example 1) as a reverse primer for BLV detection. Note that in the forward primer, the base M is a degenerate base representing A and C, the base N is a degenerate base representing A, C, G, and T, the base Y is a degenerate base representing C and T, the base K is a degenerate base representing G and T, and the base D is a degenerate base representing A, G, and T, and degeneracy of the forward primer is 1536. Note that a liquid product was used as the forward primer and a liquid product was used as the reverse primer.

TABLE 2

| No. | Sequence | Mixture ratio | Remark |
|---|---|---|---|
| 6-1 | CACCCTGAGCTGCTGCACCTCACCT | 1 | Corresponding to SEQ ID NO: 1 |
| 6-2 | MNMYCYKDAGCTGCTGAYYTCACCT | 8 | Corresponding to SEQ ID NO: 2. Degenerate primer which specifies only different bases as a degenerate base in a group made up of SEQ ID NOs: 3 to 12. |

<Preparation of Analyte for Real-Time PCR>

Prepared were (i) analytes ($1\times10^1$ mol/μL (10 copy) to $1\times10^5$ mol/μL ($10^5$ copy)) obtained by diluting, by 100-fold to 1,000,000-fold, a stock of $1\times10^7$ mol/μL ($10^7$ copy) of 1 cut calibration curve plasmid which was prepared in Reference Example 1 and concentration of which was known, (ii) a highly-concentrated analyte (HA) for real-time PCR, and (iii) 50 ng/μL of an analyte obtained by diluting the HA by 10-fold to 1,000-fold with use of genome DNA of cattle from which no BLV was detected.

<Reaction Conditions for Real-Time PCR and Data Analysis Conditions>

Real-time PCR and data analysis were conducted under reaction conditions and data analysis conditions similar to those of Reference Example 1, except that reaction reagents for real-time PCR which were used had compositions shown in Table. 3.

TABLE 3

| Reagent | x1 (μl) | Final concentration |
|---|---|---|
| Forward Primer for BLV (85 μM) | 0.20 | 850 nM |
| Reverse Primer for BLV (8.5 μM) (SEQ ID NO: 14) | 0.20 | 85 nM |
| Probe for BLV (10 μM) (SEQ ID NO: 16) | 0.30 | 150 nM |
| 2× TaqMan Gene Expression Master Mix | 10.00 | 1× |
| Sterilized water (DNase/RNase free) | 6.30 | — |
| Plasmid for Calibration Curve or Control sample (50 ng/μl) | 3.00 | 150 ng |

Total Volume: 20.00

<Results>

Figure 3:
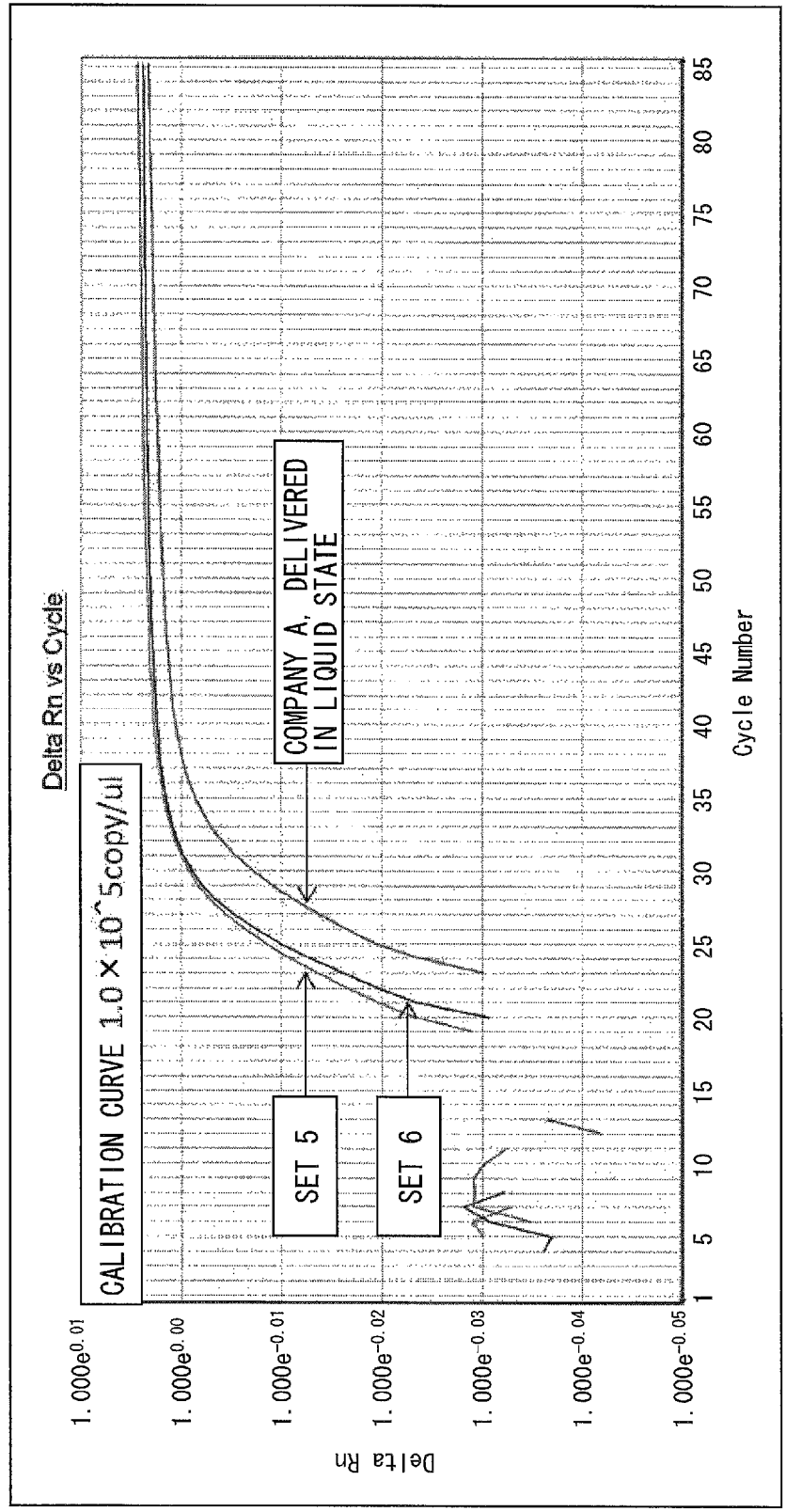
FIG. 3 is a view showing an amplification plot in Example 1.

FIG. 3 shows a relation (amplification plot) between the number of cycles (cycle number) of the real-time PCR (horizontal axis) and delta-Rn (vertical axis). FIG. 3 shows comparison between (i) a liquid product of the company A (indicated as 'COMPANY A, DELIVERED IN LIQUID STATE' in FIG. 3), which exhibits the highest quality in Reference Example 1 and (ii) the sets 5 and 6 described above.

Results of measuring Ct (Threshold cycle) values are shown in Tables. 4 and 5 below.

TABLE 4

| | Company A, delivered as liquid | Set 5 | Set 6 |
|---|---|---|---|
| $1.0 \times 10^5$ copy/μl | 28.0471 | 25.124 | 24.922 |
| $1.0 \times 10^4$ copy/μl | 31.6429 | 29.0332 | 28.822 |
| $1.0 \times 10^3$ copy/μl | 35.5501 | 33.02 | 32.65 |
| $1.0 \times 10^2$ copy/μl | 39.4191 | 36.8706 | 36.2172 |
| $1.0 \times 10^1$ copy/μl | 43.6068 | 40.0664 | 40 |

TABLE 5

| | Company A, delivered as liquid | Set 5 | Set 6 |
|---|---|---|---|
| HA | 29.0545 | 26.4443 | 26.2705 |
| MA | 33.204 | 30.4787 | 30.1721 |
| LA | 36.9724 | 33.89 | 33.86 |
| LLA | 40 | 37 | 37.93 |

*MA is obtained by diluting the HA (highly-concentrated analyte) by 10-fold, LA is obtained by diluting the HA by 100-fold, and LLA is obtained by diluting the HA by 1,000-fold As shown in FIG. 3 and Tables. 4 and 5, each of the sets 5 and 6 had a quality higher than that of the liquid product of the company A.

Example 2

A gene fragment of BLV was amplified by real-time PCR reaction under the following conditions with use of (i) a mixture of Nos. 6-1 and 6-2 (set 6) of Table. 2 below as a forward primer for BLV detection and (ii) the sequence of SEQ ID NO: 14 as a reverse primer for BLV detection. Note that the set 6 was prepared in four lots including the ones used in Example 1.

<Preparation of Analyte for Real-Time PCR>

In a similar manner as Example 1, analytes ($1\times10^1$ mol/μL (10 copy) to $1\times10^5$ mol/μL ($10^5$ copy)) were prepared by diluting, by 100-fold to 1,000,000-fold, a stock of $1\times10^7$ mol/μL ($10^7$ copy) of 1 cut calibration curve plasmid whose concentration was known.

<Reaction Conditions for Real-Time PCR and Data Analysis Conditions>

By using, as reaction reagents for real-time PCR, the reagents with the compositions of Table. 3 above, PCR reaction was conducted in such a manner that a reaction was conducted at 50° C. for two min, then at 95° C. for 10 min, and then 85 cycles of reaction, each cycle made up of a reaction at 95° C. for 15 sec and a reaction at 60° C. for one (1) min, were conducted. Except for this point, the same reaction conditions and data analysis conditions as those in Reference Example 1 were employed.

<Results>

Results of measuring Ct values are shown in Table. 6 below.

TABLE 6

|  | Example 1 | | Lot. D | | Lot. E | | Lot. F | |
|---|---|---|---|---|---|---|---|---|
| $1.0 \times 10^5$ copy/μL | 25.9572 | 25.8679 | 26.0165 | 26.0188 | 26.0279 | 26.0016 | 25.9405 | 25.8573 |
| $1.0 \times 10^4$ copy/μL | 29.9858 | 29.8208 | 29.9131 | 29.902 | 29.9672 | 29.8919 | 29.9174 | 29.8322 |
| $1.0 \times 10^3$ copy/μL | 33.5733 | 33.7374 | 33.9546 | 33.8536 | 33.9748 | 33.826 | 33.8833 | 33.7863 |
| $1.0 \times 10^2$ copy/μL | 37.5501 | 37.6031 | 37.557 | 37.9465 | 37.9824 | 37.7012 | 37.998 | 37.4638 |
| $1.0 \times 10^1$ copy/μL | 41.1314 | 43.0211 | 41.4336 | 42.2026 | 42.4903 | 41.8372 | 42.2343 | 41.1747 |

As shown in Table. 6, the set 6 had little variation among the lots.

Example 3

A gene fragment of BLV was amplified by real-time PCR reaction under the following conditions with use of (i) a mixture of Nos. 7-1 and 7-2 (set 7: SEQ ID NOs: 17 and 18) below as a forward primer for BLV detection and (ii) the sequence of SEQ ID NO: 19 (TTGCCTTACCTGMCSS-CTKSCGGATAGCCGA) as a reverse primer for BLV detection. The amplification of the gene fragment of BLV was conducted under conditions identical to those in Examples 1 and 2, except that the set 6 described in Examples 1 and 2 was used as the forward primer. Note that analytes were prepared so that the mixture ratios as shown in Table. 7 of the primers included in the set 7 were achieved.

No. 7-1:
5'-AATCCMNMYCYKDAGCTGCTGAYYTCACCT-3'
(SEQ ID NO: 17)

-continued

No. 7-2:
(SEQ ID NO: 18)
5'-ATCCACACCCTGAGCTGCTGCACCTCACCT-3'

<Preparation of Analyte for Real-Time PCR>

In a similar manner as Example 1, analytes ($1\times10^1$ mol/μL (10 copy) to $1\times10^5$ mol/μL ($10^5$ copy)) were prepared by diluting, by 100-fold to 1,000,000-fold, a stock of $1\times10^7$ mol/μL ($10^7$ copy) of 1 cut calibration curve plasmid whose concentration was known. Further, an analyte (LA) was prepared by diluting the highly-concentrated analyte (HA) for real-time PCR by 100-fold.

<Reaction Conditions for Real-Time PCR and Data Analysis Conditions>

By using, as reaction reagents for real-time PCR, the reagents with the compositions of Table. 3 above, PCR reaction was conducted in such a manner that a reaction was conducted at 50° C. for two min, then at 95° C. for 10 min, and then 60 cycles of reaction, each cycle made up of a reaction at 95° C. for 15 sec and a reaction at 60° C. for 30 sec, were conducted. Except for this point, the same reaction conditions and data analysis conditions as those in Reference Example 1 were employed.

<Results>

FIG. 4 shows a relation (amplification plot) between the number of cycles (cycle number) of real-time PCR (horizontal axis) and delta-Rn (vertical axis). Results of measuring Ct values are shown in Table. 7 below.

TABLE 7

| | <CT value> | | | | | | | | |
|---|---|---|---|---|---|---|---|---|---|
| | Mixture ratio of set 6 (6-1:6-2) | | Mixture ratio of set 7 (7-1:7-2) | | | | | | |
| | 10:1 | | 10:1 | 50:1 | 100:1 | 200:1 | 400:1 | 800:1 | 1536:1 |
| $1.0 \times 10^5$ copy/μL | 27.1763 | 27.1528 | 25.6638 | 25.6921 | 25.6076 | 25.8491 | 25.7227 | 26 | 25.6129 | 25.5523 |
| $1.0 \times 10^4$ copy/μL | 31.4822 | 31.2192 | 29.6446 | 29.7383 | 29.4621 | 29.7453 | 29.7512 | 29.8239 | 29.5347 | 29.5823 |
| $1.0 \times 10^3$ copy/μL | 35.4917 | 35.4356 | 33.5995 | 33.6855 | 33.4692 | 33.793 | 33.7712 | 33.8788 | 33.4898 | 33.5929 |
| $1.0 \times 10^2$ copy/μL | 39.0345 | 39.2433 | 37.2125 | 37.9767 | 37.0887 | 37.6143 | 37.3405 | 37.5806 | 34.0664 | 37.6663 |
| $1.0 \times 10^1$ copy/μL | 42.7119 | 42.6827 | 41.2332 | 42.2829 | 40.7961 | 40.8956 | 41.2835 | 41.7777 | 40.4 | 41.8691 |
| LA | 36.956 | 37 | 35.2502 | 35.5862 | 35.1996 | 35.4107 | 35.1819 | 35.438 | 35.2296 | 35.238 |
| Plasmid DNA containing SEQ ID NO: 1 | 33.6766 | 33.7043 | 29.0806 | 29.0932 | 28.9783 | 29.481 | 29.5023 | 29.6489 | 29.3363 | 29.5474 |

As shown in FIG. 4 and Table. 7, the set 7 is better than the set 6 in that the set 7 has lower Ct values, and a great change in mixture ratio of the primers does not affect the CT values very much.

INDUSTRIAL APPLICABILITY

The present invention is applicable to detection of BLV.

The invention claimed is:

1. A primer set capable of amplifying, through polymerase chain reaction, a DNA fragment derived from bovine leukemia virus, consisting of a combination of a forward primer and a reverse primer,
wherein the forward primer is a mixture of (1) a first primer consisting of a polynucleotide including 15 or more successive bases including the 16th cytosine in the base sequence of SEQ ID NO: 1 and (2) a second primer consisting of a plurality of polynucleotides including at least the first to 15th bases in the base sequence of SEQ ID NO: 2,
in the SEQ ID NO: 2, a base M representing A or C, a base N representing A, C, G, or T, a base Y representing C or T, a base K representing G or T, a base D representing A, G, or T,
two or more bases among the base M, the base N, the base Y, the base K, and the base D which are included in the second primer each being a degenerate base which specifies two or more bases, the plurality of polynucleotides of the second primer including at least polynucleotides including at least the first to 15th bases in the base sequences of SEQ ID NOs: 3, 4, 5, 6, 7, 8, 9, 10, 11, and 12,
wherein the reverse primer is a primer that is capable of hybridizing with the DNA fragment derived from bovine leukemia virus and amplifying the DNA fragment having a predetermined size through PCR.

2. The primer set according to claim 1, wherein each of the base M, the base N, the base Y, the base K, and the base D included in the second primer is a degenerate base which specifies all the possible bases.

3. The primer set according to claim 1, wherein the plurality of second primer consists of a plurality of different polynucleotides, each of said polynucleotides including at least the first to 18th bases in the base sequence of SEQ ID NO: 2.

4. A kit for detecting bovine leukemia virus, comprising a primer set according to claim 1.

5. A method for detecting bovine leukemia virus, comprising the steps of: (a) preparing, from a subject sample, an analyte containing DNA; (b) performing polymerase chain reaction on the analyte with use of a primer set according to claim 1; and (c) detecting an amplified fragment obtained by the step (b).

6. The primer set according to claim 1,
wherein the reverse primer is polynucleotide which includes at least 7th to 14th bases in the base sequence of SEQ ID NO: 14 and has a length of not less than 15 base length but less than 50 base length,
wherein the degenerate base S represents G or C.

* * * * *